US009888634B1

(12) United States Patent
Weiner et al.

(10) Patent No.: US 9,888,634 B1
(45) Date of Patent: Feb. 13, 2018

(54) WATER IRRIGATION RESTRICTION VIOLATION SYSTEM AND ASSOCIATED METHODS

(71) Applicant: Harris Corporation, Melbourne, FL (US)

(72) Inventors: Allan M. Weiner, Melbourne, FL (US); Brian J. Haman, West Melbourne, FL (US); William J. Sturges, Indialantic, FL (US); John E. Faure, Melbourne Beach, FL (US); James A. Bardgett, Oviedo, FL (US)

(73) Assignee: HARRIS CORPORATION, Melbourne, FL (US)

( * ) Notice: Subject to any disclaimer, the term of this patent is extended or adjusted under 35 U.S.C. 154(b) by 0 days.

(21) Appl. No.: 15/233,203

(22) Filed: Aug. 10, 2016

(51) Int. Cl.
G08B 21/00 (2006.01)
A01G 25/16 (2006.01)
(Continued)

(52) U.S. Cl.
CPC ............ *A01G 25/167* (2013.01); *G01J 1/429* (2013.01); *G01J 5/10* (2013.01); *G01N 21/55* (2013.01); *G06K 9/00657* (2013.01); *G08B 21/182* (2013.01); *G01J 2005/0077* (2013.01); *G01N 2201/12* (2013.01); *G06K 2009/00644* (2013.01); *G06Q 50/26* (2013.01)

(58) Field of Classification Search
None
See application file for complete search history.

(56) References Cited

U.S. PATENT DOCUMENTS 9,652,840 B1 * 5/2017 Shriver ................. G06T 7/0004
2011/0049260 A1 * 3/2011 Palmer ................... A01G 25/16
239/63
(Continued)

FOREIGN PATENT DOCUMENTS

CN 203643441 6/2014
CN 204346493 5/2015
CN 104848893 8/2015

OTHER PUBLICATIONS

Allen et al. Evapotranspiration from landsat (SEBAL) for water rights management and compliance with mulit-state water compacts. Geoscience and Remote Sensing Symposium, 2001. IGARSS '01. IEEE 2001 International (vol. 2 ) pp. 830-833 vol. 2.
(Continued)

*Primary Examiner* — Adolf Dsouza
(74) *Attorney, Agent, or Firm* — Allen, Dyer, Doppelt, + Gilchrist, P.A. Attorneys at Law

(57) ABSTRACT

A water irrigation restriction violation system includes a geostationary satellite to collect soil surface moisture data and rain data throughout a given day for a geographic region. A processor and a memory coupled to the processor are configured to store water irrigation restrictions for governmental jurisdictions for the geographic region, receive the soil surface moisture data and rain data from the geostationary satellite, and determine a water irrigation restriction violation based upon the stored water irrigation restrictions and the received soil surface moisture data and rain data. A violation notification is then sent to a corresponding governmental jurisdiction for the determined water irrigation restriction violation.

24 Claims, 5 Drawing Sheets

(51) Int. Cl.
*G01J 5/10* (2006.01)
*G01N 21/55* (2014.01)
*G01J 1/42* (2006.01)
*G06K 9/00* (2006.01)
*G08B 21/18* (2006.01)
*G01J 5/00* (2006.01)
*G06Q 50/26* (2012.01)

(56) References Cited

U.S. PATENT DOCUMENTS

| | | | | |
|---|---|---|---|---|
| 2011/0093123 | A1* | 4/2011 | Alexanian | A01G 25/16 700/284 |
| 2011/0190947 | A1* | 8/2011 | Savelle, Jr. | G05D 11/02 700/284 |
| 2011/0295575 | A1* | 12/2011 | Levine | G06Q 30/02 703/2 |
| 2011/0301767 | A1 | 12/2011 | Alexanian | |
| 2011/0307177 | A1 | 12/2011 | Hong | |
| 2012/0101861 | A1* | 4/2012 | Lindores | G06Q 10/06 705/7.11 |
| 2012/0239211 | A1* | 9/2012 | Walker | G05B 13/021 700/284 |
| 2014/0369568 | A1* | 12/2014 | Mangoubi | G06T 7/41 382/108 |
| 2015/0223416 | A1* | 8/2015 | Eng | A01G 25/167 700/284 |
| 2016/0202679 | A1* | 7/2016 | Bermudez Rodriguez | G05B 19/042 700/284 |

OTHER PUBLICATIONS

Dabrowska-Zielinska et al. Application of various satellite derived information for drought detection and calculation of water balance http://spie.org/Publications/Proceedings/Paper/10.1117/12.693754?print=2; Dec. 12, 2006; Abstract Only.

Viau et al. "Comparison of a Satellite-based and a precipitation-based drought index" Canadian Journal of Remote Sensing 26(6):580-583 • Jul. 2014; Abstract Only.

Sahoo et al. "Evaluation of the Tropical Rainfall Measuring Mission Multi-Satellite Precipitation Analysis (TMPA) for assessment of large-scale meteorological drought" Remote Sensing of Environment: vol. 159, Mar. 15, 2015, pp. 181-193; http://www.sciencedirect.com/science/article/pii/S003442571400488X; Abstract Only.

Pullanagari et al. "Multi-spectral radiometry to estimate pasture quality components" Precision Agriculture 13(4) Aug. 2012: https://www.researchgate.net/publication/257640199_Multi-spectral_radiometry_to_estimate_pasture_quality_components; pp. 18.

Anderson et al. "Mapping daily evapotranspiration at field to continental scales using geostationary and polar orbiting satellite imagery" (Hydrology and Earth System Sciences, v 15, n 1, p. 223-239, 2011).

Boussetta et al. "Assimilation of surface albedo and vegetation states from satellite observations and their impact on numerical weather prediction" Remote Sensing of Environment 163 • Apr. 2015: pp. 19.

Karen Greer "The Constitutionality of Remote Sensing Satellite Surveillance in warrantless Environmental Inspections" Fordham Environmental Law Review; vol. 3, Issue 1 2011 Article 3; pp. 15.

Pierdicca et al. "A multistatic radar approach to soil moisture and vegetation monitoring at L band" 2015 IEEE International Geosoience and Remote Sensing Symposium (IGARSS): Jul. 26-31, 2015; http://ieeexplore.ieee.org/xpl/login.jsp?tp=&arnumber=7326977 &url=http%3A%2F%2Fieeexpiore.ieee.org%2Fxpls%2Fabs_all.jsp%3Farnumber%3D7326977: pp. 5087-6996; Abstract Only.

Van Dijk et al. "Water resource monitoring systems and the role of satellite observations" Published by Copernicus Publications on behalf of the European Geosciences Union: Revised Nov. 29, 2010—Accepted: Dec. 14, 2010—Published: Jan. 4, 2011; pp. 17.

Nirappil et al. "California flexes muscles in water tussle with farmers" http://bigstory.ap.org/article/622ab95b45ff4fb4a4798765afe09048/state-says-irrigation-district-violated-2015-drought-order: Jul. 27, 2016; pp. 5.

Dale Kasler "California drought agency goes after another water district" http://www.sacbee.com/news/state/california/water-and-drought/article27933571.html: Jul. 27, 2016 pp. 6.

Anonymous Science Benefits of Advanced Geosynchronous Observations (The Scientific Basis for the Advanced Geosynchronous Studies Program) http://goes.gsfc.nasa.gov/text/ags_science.html: Mar. 1998; pp. 21.

* cited by examiner

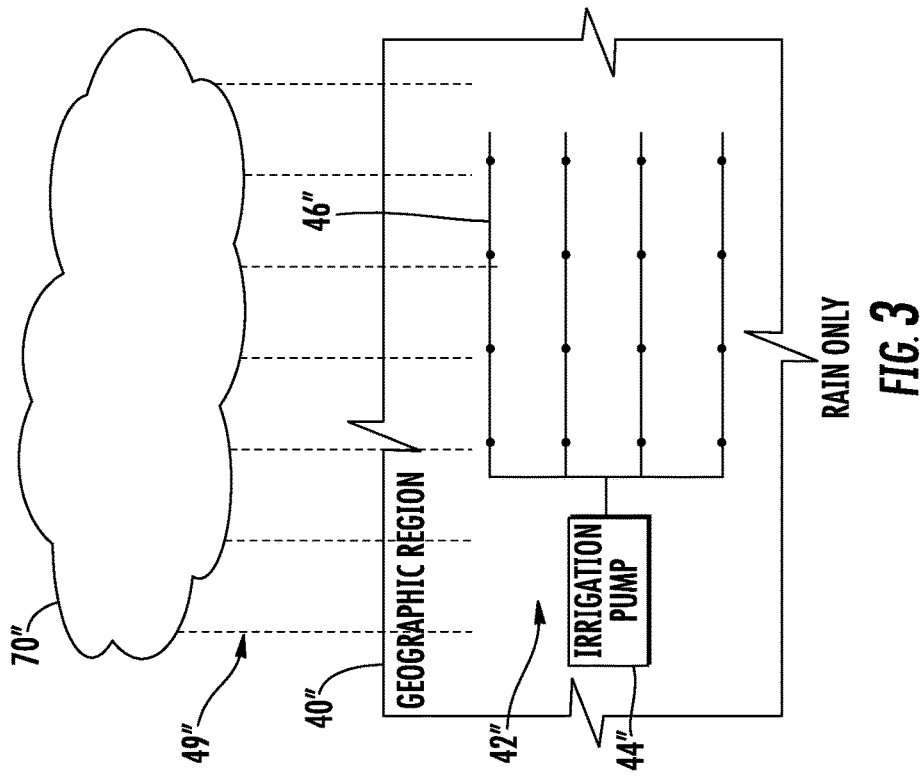
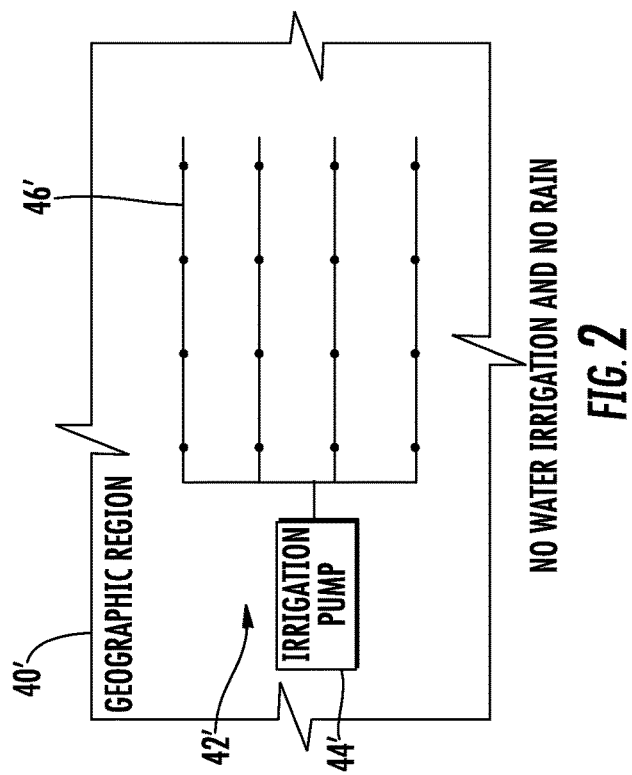

WATER IRRIGATION RESTRICTION VIOLATION SYSTEM AND ASSOCIATED METHODS

FIELD OF THE INVENTION

The present invention relates to the field of water irrigation, and more particularly, to a water irrigation restriction violation system to determine when water irrigation restrictions are violated, and related methods.

BACKGROUND

One of the main purposes of water irrigation is to grow crops. Unlike some states in the Midwest, certain geographic regions in California, for example, do not receive enough rain during the summer. This makes water irrigation a necessity.

Agricultural irrigation districts in California utilize local rivers, and store the water in reservoirs. The irrigation season usually runs from approximately March 15 to October 15, depending on the weather and water supplies.

Even in geographical regions other than in California, severe drought is causing local governmental jurisdictions to issue water irrigation restrictions. Water irrigation restrictions are typically in the form of allowed or not allowed watering days of the week, and/or times of the day.

Discovery of water irrigation restriction violations is difficult due to the large land areas involved and the transient nature of "wet" soil. One approach is for local authorities to use drones to patrol the geographical regions subjected to water irrigation restrictions. A drawback of using drones is that it is cost prohibitive to provide around the clock aerial coverage due to manpower and equipment costs.

Another aerial approach is to use satellites. Even though the use of satellites may be economically viable, a drawback is that the same geographical region is not observed often enough. Soil surfaces may dry between satellite passes, for example. In addition, the spatial resolution of the satellites is typically too coarse.

Consequently, there is a need to help governmental jurisdictions to discourage local agribusinesses from violating water irrigation restrictions.

SUMMARY

A water irrigation restriction violation system includes at least one geostationary satellite configured to collect soil surface moisture data and rain data a plurality of times in a given day for a geographic region. The water irrigation restriction violation system may further include a processor and a memory coupled thereto and configured to store water irrigation restrictions for a plurality of governmental jurisdictions for the geographic region, and receive the soil surface moisture data and rain data from the at least one geostationary satellite. A water irrigation restriction violation may then be determined based upon the stored water irrigation restrictions and the received soil surface moisture data and rain data. A violation notification may be sent to a corresponding governmental jurisdiction for the determined water irrigation restriction violation.

The soil surface moisture data and rain data may be based on images obtained by the geostationary satellite. The images may have a spatial resolution of 0.5 to 2 km, for example. The geostationary satellite may comprise at least one infrared image sensor and at least one visible light image sensor to collect the soil surface moisture data and rain data.

The geostationary satellite may collect the soil surface moisture data at least every 15 minutes.

Areas of the geographic region subjected to water irrigation restrictions may now be viewed by the geostationary satellite on a routine basis with short time periods between each viewing, and with good spatial resolution, so that wet soil can advantageously be observed before the top layer dries out. The violation notifications received by governmental jurisdictions may be used to discourage local agribusinesses from violating water irrigation restrictions.

The processor may determine the water irrigation restriction violation by at least determining an exceedance of the soil surface moisture data relative to a soil surface moisture threshold; determining, based upon the rain data, when irrigation, not rain, caused the exceedance; determining a day of the exceedance caused by irrigation and not rain; and comparing the day of the exceedance to the water irrigation restrictions. The soil surface moisture threshold may be qualitative or quantitative.

The processor may further determine the water irrigation restriction violation by at least determining a time-of-day of the exceedance caused by irrigation and not rain; and comparing the time-of-day of the exceedance to the water irrigation restrictions.

The violation notification may include an image of the geographical region where the determined water irrigation restriction violations occurred. The violation notification may further includes a data and a time-of-day associated with the image.

The water irrigation restrictions may be based on dates and times-of-day. The geostationary satellite may comprise a geostationary operational environmental satellite (GOES). More particularly, the geostationary operational environmental satellite (GOES) may comprise an R series geostationary operational environmental satellite (GOES-R).

Another aspect is directed to a water irrigation restriction violation system comprising an interface configured to receive from at least one geostationary satellite soil surface moisture data and rain data a plurality of times in a given day for a geographic region. The water irrigation restriction violation processing system may also comprise a processor and a memory coupled thereto and configured to perform the steps as described above.

Yet another aspect is directed to a method for operating the water irrigation restriction violation system as discussed above. The method comprises collecting soil surface moisture data and rain data from at least one geostationary satellite a plurality of times in a given day for a geographic region. The method may further include storing water irrigation restrictions for a plurality of governmental jurisdictions for the geographic region, and receiving the soil surface moisture data and rain data from the at least one geostationary satellite. A water irrigation restriction violation may be determined based upon the stored water irrigation restrictions and the received soil surface moisture data and rain data. A violation notification is sent to a corresponding governmental jurisdiction for the determined water irrigation restriction violation.

BRIEF DESCRIPTION OF THE DRAWINGS

FIGS. 2-4 are schematic perspective views illustrating different conditions of the geographic region in FIG. 1.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements.

Figure 1:
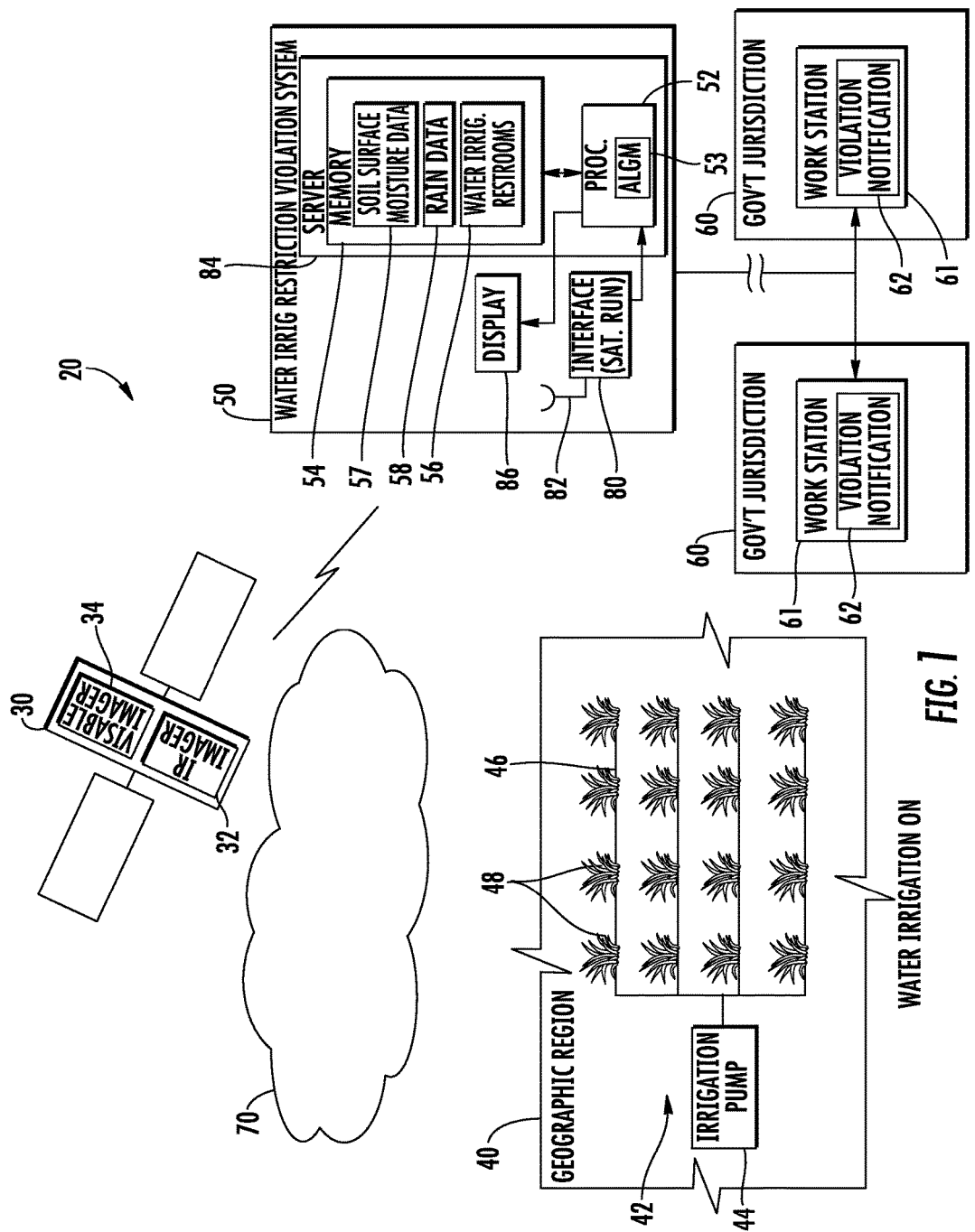
FIG. 1 is a schematic block diagram of a water irrigation restriction violation system for a geographic region in accordance with the present invention.

Referring initially to FIG. 1, a water irrigation restriction violation system 20 will be discussed. The water irrigation restriction violation system 20 includes at least one geostationary satellite 30 to regularly collect soil surface moisture data 57 and rain data 58 throughout a given day for a geographic region 40, and a ground-based water irrigation restriction violation system 50 for processing the collected soil surface moisture data and rain data.

The ground-based water irrigation restriction violation system 50 includes a processor 52 and a memory 54 coupled to the processor. The processor 52 and memory 54 are configured to store water irrigation restrictions 56 for a number of different governmental jurisdictions 60 for the geographic region 40, receive the soil surface moisture data 57 and rain data 58 from the geostationary satellite 30, determine a water irrigation restriction violation based upon the stored water irrigation restrictions 56 and the received soil surface moisture data 57 and rain data 58, and send a violation notification 62 to a corresponding governmental jurisdiction 60 for the determined water irrigation restriction violation.

The illustrated geostationary satellite 30 collects the soil surface moisture data and rain data 58 least every 15 minutes, for example, and at a spatial resolution of 0.5 to 2 km, for example. The geostationary satellite 30 includes at least one infrared image sensor 32 and at least one visible light image sensor 34 to provide images of the geographical region 40.

Areas of the geographic region 40 subjected to water irrigation restrictions may now be viewed by the geostationary satellite 30 on a routine basis with short time periods between each viewing, and with good spatial resolution, so that wet soil can advantageously be observed before the top layer dries out. The violation notifications 62 received by governmental jurisdictions 60 may be used to discourage local agribusinesses from violating water irrigation restrictions.

The illustrated geostationary satellite 30 may be a geostationary operational environmental satellite-R series (GOES-R) spacecraft, which is scheduled to be launched in 2016. The GOES spacecraft is for imaging earth's weather, oceans and environment. The GOES-R spacecraft provides three times more spectral information, four times the spatial resolution, and more than five times faster temporal coverage than the current GOES spacecraft. In addition, other series of GOES spacecraft are scheduled to be launched into orbit. An S series is scheduled to be launched in 2017, a T series is scheduled to be launched in 2019, and a U series is scheduled to be launched in 2025. Other spacecraft, now in the planning stages, may also include hyperspectral information with hundreds of times more spectral information than the current imagers.

The water irrigation restriction violation system 20 is not limited to the GOES series spacecraft. Other environmental satellites providing similar temporal resolution and spatial resolution may be used, as readily appreciated by those skilled in the art.

The GOES-R spacecraft includes an advanced baseline imager (ABI) to view the earth with 16 different spectral bands. The 16 different spectral bands include 2 visible channels, 4 near-infrared channels, and 10 infrared channels.

More particularly, the ABI is a passive imaging radiometer designed to observe the western hemisphere and provide variable area imagery and radiometric information of the earth's surface, atmosphere and cloud cover. The ABI will be used for a wide range of applications related to weather, oceans, lands, climate and hazards.

The ABI has 2 scan modes. One mode is the full disk (FD) scan mode which continuously takes an image of the western hemisphere every 5 to 15 minutes and at a spatial resolution of 0.5 to 2 km. Another mode is the flex mode, which will concurrently take a FD image every 15 minutes, an image of the continental U.S. every 5 minutes, and smaller, more detailed images of areas where storm activity is present, as often as every 30 seconds. The flex mode also has a spatial resolution of 0.5 to 2 km.

Still referring to FIG. 1, the geographic region 40 includes a water irrigation system 42. The water irrigation system 42 includes a water irrigation pump 44 that provides water 48 to irrigation lines 46 coupled to the water irrigation pump. Operation of the water irrigation system 42 may be based on water irrigation restrictions 56 as determined by a government municipality or jurisdiction 60. The water irrigation restrictions 56 are based on dates and times-of-day. The dates include allowed and not allowed watering days, and the times-of-day include allowed and not allowed watering times.

As noted above, the geostationary satellite 30 collects soil surface moisture data 57 and rain data 58 a number of times in a given day for the geographic region 40. For a GOES-R spacecraft, the soil surface moisture data 57 and rain data 58 may be collected every 5 to 15 minutes and at a spatial resolution of 0.5 to 2 km.

The soil surface moisture data 57 and rain data 58 are based on images received by the geostationary satellite 30. The visible light imager 34 carried by the geostationary satellite 30 provides black and white photographs of the geographic region 40. Clouds 70 usually appear white, while land and water surfaces of the geographic region 40 appear in shades of gray and black. Pixel intensity values of the received images are used to provide the soil surface moisture data 57, as readily appreciated by those skilled in the art.

The visible light imager 34 senses reflected solar radiation. Clouds, the earth's atmosphere, and the earth's surface all absorb and reflect incoming solar radiation. Since visible imagery is produced by reflected sunlight, it is only available during daylight.

One of the advantages of visible imagery is that it has a higher resolution (about 0.5 km) than infrared images (about 2 km), so smaller features can be distinguished. The pixel intensity values of the different shades of gray and black in the received images are used by the processor 52 to estimate the soil surface moisture data 57 for the geographic region 40. The soil surface moisture threshold may be qualitative or quantitative.

The infrared imager 32 carried by the geostationary satellite 30 senses energy as heat. The earth's surface absorbs about half of the incoming solar energy. Clouds and the atmosphere absorb a much smaller amount. The earth's surface, clouds, and the atmosphere then re-emit part of this absorbed solar energy as heat. The infrared images provided by the infrared imager 32 are thus based on the re-emitted radiation.

As with the visible imagery, the pixel intensity values of the different shades of gray and black in the infrared imagery are used to estimate the soil surface moisture data 57. One of the advantages of infrared imagery is that it is available at night as well as being available in the daylight. Consequently, the infrared imagery is available throughout the day and night. The pixel intensity values of different shades of gray and black of the individual bands in the received images as well as combinations of bands by the server 52 are used by the processor 52 to estimate the soil surface moisture data 57 (either qualitative or quantitative) for the geographic region 40.

The rain data 58 for the geographic region 40 is separate from the soil surface moisture data 57, and is based on the detection of clouds. The rain data 58 may be subdivided by cloud type, as indicated by selected brightness temperature differences, as readily appreciated by those skilled in the art. For example, there are water clouds, ice clouds, and cold-top convective clouds, each with their selected brightness temperature differences.

The rain data 58 may also account for differences in the relationship between cloud-top properties and rainfall rate. The amount of rain data 58 may be based on the number of pixels with non-zero rain rates.

For discussion purposes, the GOES-R spacecraft includes a rainfall rate algorithm based on a self-calibrating multivariate precipitation retrieval (SCaMPR). The rainfall rate algorithm calibrates predictors against rainfall rates and then applies the resulting relationships to the collected data to provide rainfall estimates that are continuously available but more accurate than estimates based on IR data with a fixed calibration.

The ground-based water irrigation restriction violation system 50 illustrated in FIG. 1 includes an interface 80 to receive the images obtained by the geostationary satellite 30. The interface 80 is coupled to the processor 52. In one embodiment, the interface 80 is a satellite receiver coupled to a dish antenna 82, as illustrated in FIG. 1. Alternatively, the interface 80 may be coupled to the Internet or a telephone line, for example.

The processor 52 and the memory 54 form a server 84. The collected soil surface moisture data 57 and rain data 58 are stored in the memory 54. The water irrigation restrictions 56 for the different governmental jurisdictions of the geographic region 40 are also stored in the memory 54.

The water irrigation restriction violation processing system 50 may further include a display 86 to display images received by the satellite receiver 80 and processed by the processor 52. The processor 52 executes an algorithm 53 in real time to determine a water irrigation restriction violation based upon the stored water irrigation restrictions 56 and the collected soil surface moisture data 57 and rain data 58.

A violation notification 62 is sent to a corresponding governmental jurisdiction 60 for the determined water irrigation restriction violation. More particularly, the illustrated violation notification 62 is received by a work station 61 at the corresponding governmental jurisdiction 60. Each governmental jurisdiction 60 will have its own work station 61. The violation notification 62 may further include images of the geographical region 40 where the determined water irrigation restriction violation occurred. The images may also have a date and a time-of-day associated therewith.

Referring now to FIGS. 2-5, a method for operating the water irrigation restriction violation system 20 as discussed above will be discussed. Operation of the water irrigation restriction violation system 20 takes into account different conditions of the geographic region 40. Each of the different conditions effects the collected soil surface moisture data 57 and rain data for the geographic region 40, as readily appreciated by those skilled in the art.

Figure 4:
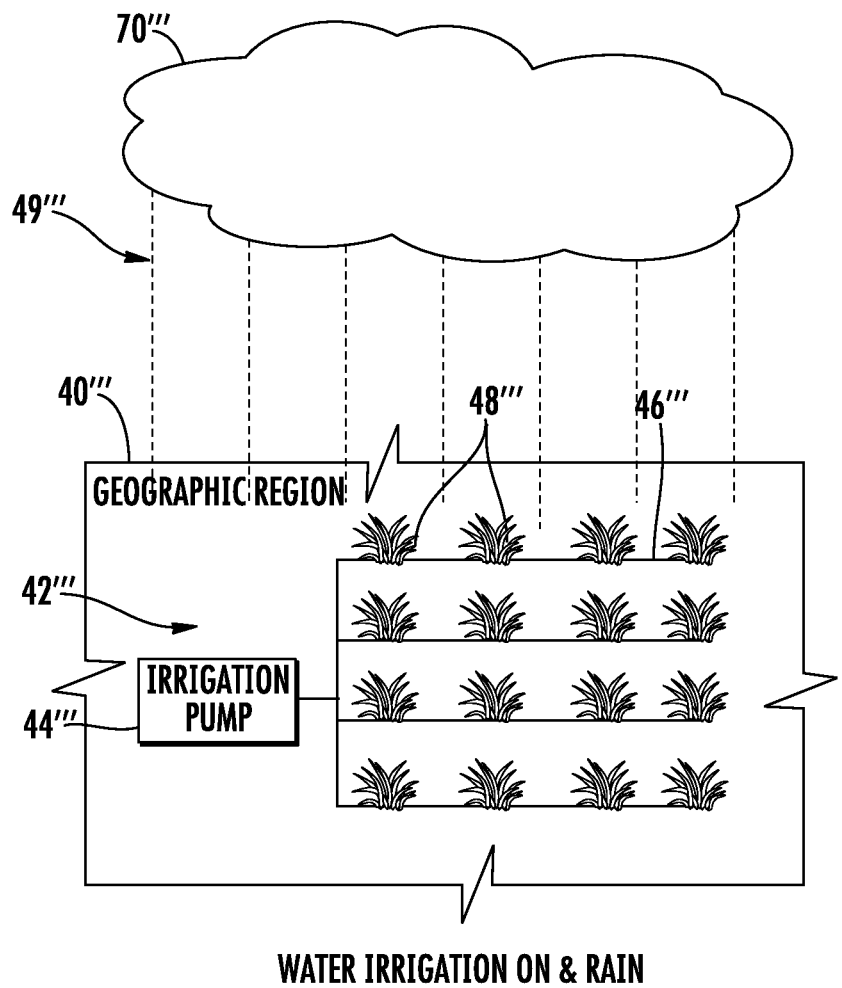

As illustrated in FIG. 1, the water irrigation system 42 is on and no rain is present. Another condition for the geographic region 40' is for the water irrigation system 42' to be off and no rain is present, as illustrated in FIG. 2. Another condition for the geographic region 40" is for the water irrigation system 42" to be off and rain is present, as illustrated in FIG. 3. Yet another condition for the geographic region 40''' is for the water irrigation system 42''' to be on and rain is present, as illustrated in FIG. 4.

Figure 5:
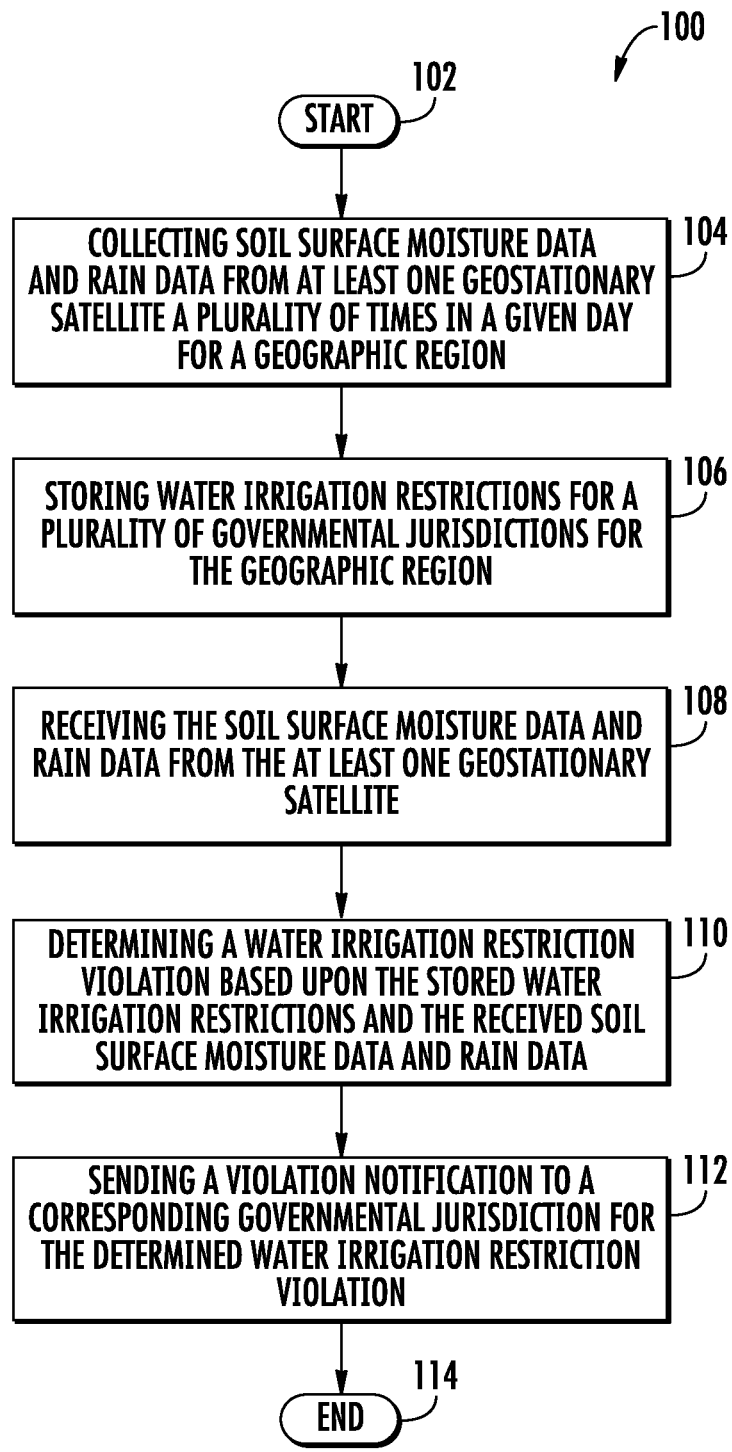
FIG. 5 is a flowchart illustrating operation of the water irrigation restriction violation system in FIG. 1.

Referring now to the flowchart 100 in FIG. 5, the method comprises, from the start (Block 102), determining an exceedance of the soil surface moisture data 57 relative to a soil surface moisture threshold at Block 104. The method includes determining, based upon the rain data 58, when irrigation, not rain, caused the exceedance at Block 106. A day of the exceedance caused by irrigation and not rain is determined at Block 108. The day of the exceedance is compared to the water irrigation restrictions 56 at Block 110. The method may further include determining a time-of-day of the exceedance caused by irrigation and not rain at Block 112. The time-of-day of the exceedance is compared to the water irrigation restrictions at Block 114. The method ends at Block 116.

Figure 6:
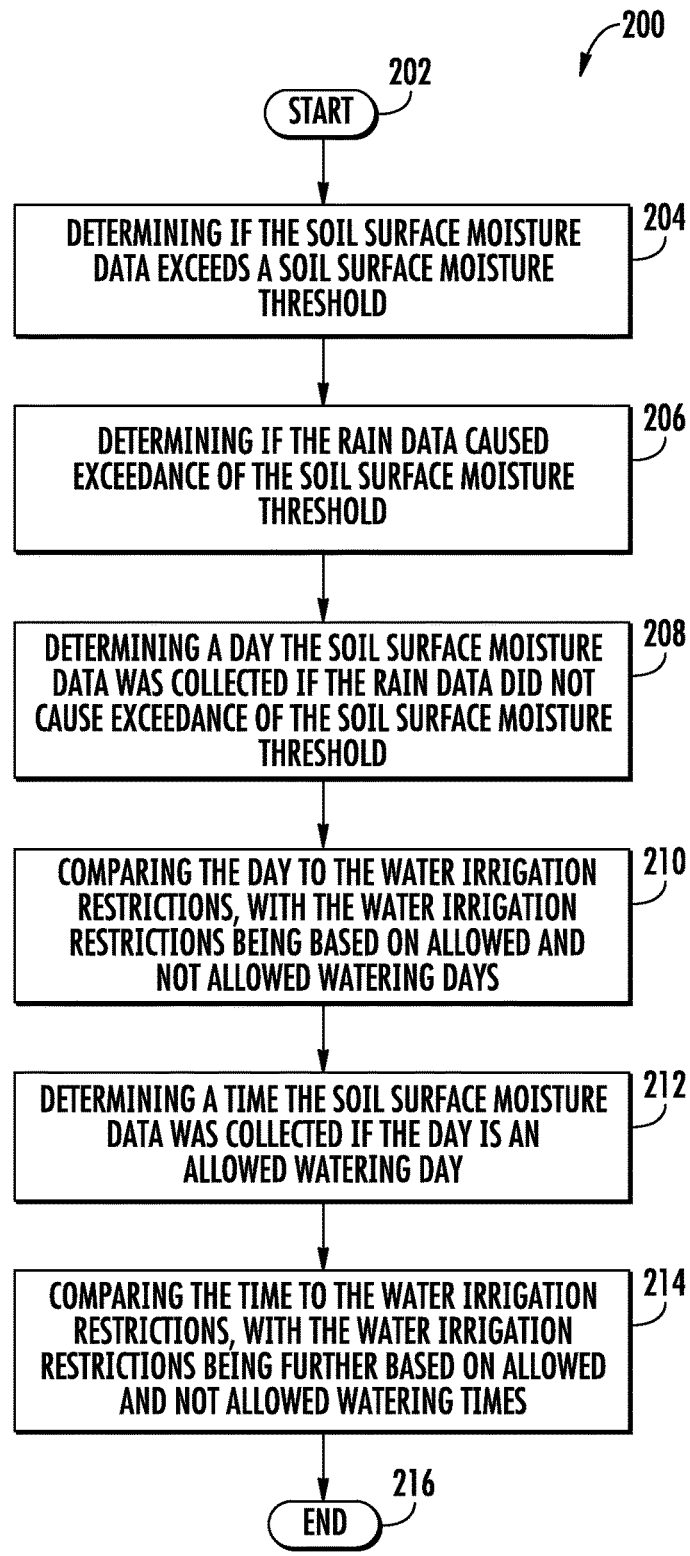
FIG. 6 is a detailed flowchart illustrating operation of the processor in FIG. 1.

A flowchart 200 directed to an algorithm 53 executed by the processor 52 to determine a water irrigation restriction violation will be discussed in reference to FIG. 6. From the start (Block 102), a determination is made at Block 204 if the soil surface moisture data 57 exceeds a soil surface moisture threshold. If the threshold is exceeded, then a determination is made if the rain data 58 caused exceedance of the soil surface moisture threshold. If the rain data 58 did not cause exceedance of the soil surface moisture threshold, then a day the soil surface moisture data 57 was collected is determined at Block 208.

The day is compared at Block 210 to the water irrigation restrictions 56, with the water irrigation restrictions being based on allowed and not allowed watering days. If the day is a not allowed watering day, then a violation notification 62 will be generated. Otherwise, if the day is an allowed watering day, then a time the soil surface moisture data 57 was collected is determined at Block 212.

The time is compared to the water irrigation restrictions 56 at Block 214, with the water irrigation restrictions being further based on allowed and not allowed watering times. If the time is not an allowed watering time, then a violation notification 62 will not be generated. Otherwise, if the time is an allowed watering time, then a violation notification 62 will not be generated. The process ends at Block 216.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A water irrigation restriction violation system comprising:
   at least one geostationary satellite configured to collect different spectral band images a plurality of times in a given day for a geographic region to generate soil surface moisture data and rain data; and
   a processor and a memory coupled thereto and configured to
      store water irrigation restrictions for a plurality of governmental jurisdictions for the geographic region,
      receive the soil surface moisture data and rain data from said at least one geostationary satellite,
      determine a water irrigation restriction violation based upon the stored water irrigation restrictions and the received soil surface moisture data and rain data by at least
         determining an exceedance of the soil surface moisture data relative to a soil surface moisture threshold,
         determining, based upon the rain data, when irrigation, not rain, caused the exceedance,
         determining a time period of the exceedance caused by irrigation and not rain, and
         comparing the time period of the exceedance to the water irrigation restrictions, and
      send a violation notification to a corresponding governmental jurisdiction for the determined water irrigation restriction violation.

2. The water irrigation restriction violation system according to claim 1 wherein said at least one geostationary satellite comprises at least one infrared image sensor and at least one visible light image sensor to collect the different spectral band images.

3. The water irrigation restriction violation system according to claim 1 wherein said at least one geostationary satellite collects the different spectral band images at least every 15 minutes.

4. The water irrigation restriction violation system according to claim 1 wherein said processor further determines the water irrigation restriction violation by at least:
   determining a time-of-day of the exceedance caused by irrigation and not rain; and
   comparing the time-of-day of the exceedance to the water irrigation restrictions.

5. The water irrigation restriction violation system according to claim 1 wherein the violation notification includes an image of the geographical region where the determined water irrigation restriction violations occurred.

6. The water irrigation restriction violation system according to claim 5 wherein the violation notification further includes a date and a time-of-day associated with the image.

7. The water irrigation restriction violation system according to claim 1 wherein the water irrigation restrictions are based on dates and times-of-day.

8. The water irrigation restriction violation system according to claim 1 wherein said at least one geostationary satellite comprises a geostationary operational environmental satellite (GOES).

9. A water irrigation restriction violation system comprising:
   an interface configured to receive from at least one geostationary satellite soil surface moisture data and rain data a plurality of times in a given day for a geographic region, the satellite soil surface moisture data and rain data being generated based upon different spectral band images collected by the at least one geostationary satellite; and
   a processor and a memory coupled thereto and configured to
      store water irrigation restrictions for a plurality of governmental jurisdictions for the geographic region,
      receive the soil surface moisture data and rain data from the at least one geostationary satellite,
      determine a water irrigation restriction violation based upon the stored water irrigation restrictions and the received soil surface moisture data and rain data by at least
         determining an exceedance of the soil surface moisture data relative to a soil surface moisture threshold,
         determining, based upon the rain data, when irrigation, not rain, caused the exceedance,
         determining a time period of the exceedance caused by irrigation and not rain, and
         comparing the time period of the exceedance to the water irrigation restrictions, and
      send a violation notification to a corresponding governmental jurisdiction for the determined water irrigation restriction violation.

10. The water irrigation restriction violation system according to claim 9 wherein said at least one geostationary satellite collects the different spectral band images at least every 15 minutes.

11. The water irrigation restriction violation system according to claim 9 wherein said processor further determines the water irrigation restriction violation by at least:
   determining a time-of-day of the exceedance caused by irrigation and not rain; and
   comparing the time-of-day of the exceedance to the water irrigation restrictions.

12. The water irrigation restriction violation system according to claim 9 wherein the violation notification includes an image of the geographical region where the determined water irrigation restriction violations occurred.

13. The water irrigation restriction violation system according to claim 12 wherein the violation notification further includes a date and a time-of-day associated with the image.

14. The water irrigation restriction violation system according to claim 9 wherein the water irrigation restrictions are based on dates and times-of-day.

15. A method for operating a water irrigation restriction violation system comprising:
   receiving soil surface moisture data and rain data from at least one geostationary satellite a plurality of times in a given day for a geographic region, the satellite soil surface moisture data and rain data being generated based upon different spectral band images collected by the at least one geostationary satellite; and
   operating a processor and a memory coupled thereto to perform the following
      store water irrigation restrictions for a plurality of governmental jurisdictions for the geographic region,
      receive the soil surface moisture data and rain data from the at least one geostationary satellite,
      determine a water irrigation restriction violation based upon the stored water irrigation restrictions and the received soil surface moisture data and rain data by at least determining an exceedance of the soil surface moisture data relative to a soil surface moisture threshold, determining, based upon the rain data, when irrigation, not rain, caused the exceedance, determining a time period of the exceedance caused by irrigation and not rain, and comparing the time period of the exceedance to the water irrigation restrictions, and send a violation notification to a corresponding governmental jurisdiction for the determined water irrigation restriction violation.

16. The method according to claim 15 wherein the at least one geostationary satellite comprises at least one infrared image sensor and at least one visible light image sensor to collect the different spectral band images.

17. The method according to claim 15 wherein the processor further determines the water irrigation restriction violation by at least:

determining a time-of-day of the exceedance caused by irrigation and not rain; and comparing the time-of-day of the exceedance to the water irrigation restrictions.

18. The method according to claim 15 wherein the violation notification includes an image of the geographical region where the determined water irrigation restriction violations occurred.

19. The method according to claim 18 wherein the violation notification further includes a date and a time-of-day associated with the image.

20. The method according to claim 15 wherein the water irrigation restrictions are based on dates and times-of-day.

21. The method according to claim 15 wherein the at least one geostationary satellite comprises a geostationary operational environmental satellite (GOES).

22. A water irrigation restriction violation system comprising:

an interface configured to receive from at least one geostationary satellite soil surface moisture data and rain data a plurality of times in a given day for a geographic region; and a processor and a memory coupled thereto and configured to store water irrigation restrictions for a plurality of governmental jurisdictions for the geographic region, receive the soil surface moisture data and rain data from the at least one geostationary satellite, determine a water irrigation restriction violation based upon the stored water irrigation restrictions and the received soil surface moisture data and rain data by at least determining an exceedance of the soil surface moisture data relative to a soil surface moisture threshold, determining, based upon the rain data, when irrigation, not rain, caused the exceedance, determining a day of the exceedance caused by irrigation and not rain, and comparing the day of the exceedance to the water irrigation restrictions, and send a violation notification to a corresponding governmental jurisdiction for the determined water irrigation restriction violation.

23. The water irrigation restriction violation system according to claim 22 wherein the soil surface moisture data and rain data are based on images obtained by the at least one geostationary satellite.

24. The water irrigation restriction violation system according to claim 22 wherein said at least one geostationary satellite collects the soil surface moisture data at least every 15 minutes.

* * * * *